United States Patent [19]

Blum

[11] Patent Number: 5,384,120
[45] Date of Patent: Jan. 24, 1995

[54] ATTRACTANTS AND LURES FOR COCKROACHES AND PALMETTOS

[75] Inventor: Mel Blum, Wantagh, N.Y.

[73] Assignee: Burlington Bio-Medical & Scientific Corp., Farmingdale, N.Y.

[21] Appl. No.: 405,613

[22] Filed: Sep. 8, 1989

[51] Int. Cl.$^6$ ............................................. A01N 25/00
[52] U.S. Cl. ............................................................ 424/84
[58] Field of Search ............................................ 424/84

[56] References Cited

U.S. PATENT DOCUMENTS

| | | | |
|---|---|---|---|
| 2,657,166 | 10/1953 | Stonecipher | 167/30 |
| 3,913,259 | 10/1975 | Nishimura | 43/114 |
| 4,386,071 | 5/1983 | Carle | 424/127 |
| 4,748,860 | 6/1988 | Butter | 73/866 |

FOREIGN PATENT DOCUMENTS

| | | | |
|---|---|---|---|
| 6030940 | 8/1979 | Japan | 424/84 |
| 9067209 | 10/1982 | Japan | 424/84 |

OTHER PUBLICATIONS

Merck Index 10th Ed #313–323 pp. 310–311, 1983.

*Primary Examiner*—Marianne M. Cintins
*Assistant Examiner*—Russell Travers
*Attorney, Agent, or Firm*—Jordan and Hamburg

[57] ABSTRACT

Propyl cyclo hexyl acetate is Utilized as an aggregation pheromone for the German cockroach and the combination of isobornyl acetate and santalol alone or in conjunction with propyl cyclo hexyl acetate is utilized for attracting the American, Oriental, Smokey Brown and Brown Banded cockroaches as well as palmettos. Also, in admixture with a known blatticide boric acid, boric oxide, calcium borate and sodium borate is used pyrogenic silica, pyrogenic titania or pyrogenic alumina, which are found to act as highly effective electrostatic agents which cause the blatticide to cling to the cockroaches or palmettos.

8 Claims, No Drawings

ATTRACTANTS AND LURES FOR COCKROACHES AND PALMETTOS

BACKGROUND OF THE INVENTION

This invention relates to attractants and baits for cockroaches and palmettos. More particularly, this invention relates to attractants and baits incorporating pheromones for cockroaches and palmettos.

The art of cockroach attractant compositions includes, for example, U.S. Pat. Nos. 4,049,460 and 4,332,782. Moreover, certain acetates have been disclosed as being sex pheromones for certain insects. For example, U.S. Pat. No. 4,734,281 relates to a method for simultaneously emitting vapors of sex pheromones of different insects; the compounds emitted are selected from a first group consisting of E,E-8,10-dodecadienol and E-5-decenol and a second group consisting of Z-8-dodecenyl acetate, 11-tetradecenyl acetate, Z,Z-3,13-octadecenyl acetate and Z,Z-11,13-hexadecadienal. Also, U.S. Pat. Nos. 3,845,108 and 3,866,349 relate to compounds which are attractants or pheromones when mixed in the correct proportions; essentially, the particular attractants are directed to a particular type moth, and the composition comprises 1 part cis-11-tetradecenyl acetate and about 3-9 parts cis-9-tetradecenyl acetate. U.S. Pat. Nos. 3,845,108, 3,991,125, 4,042,681, 4,107,293, 4,364,931 and 4,575,458 relate to attractants for moths, worms and the like, the attractants including various acetates.

SUMMARY OF THE INVENTION

According to the present invention it has been found that propyl cyclo hexyl acetate is an aggregation pheromone for the German cockroach and it has been found that the combination of isobornyl acetate and santalol alone or in conjunction with the aforementioned aggregation pheromone is effective for attracting the American, Oriental, Smokey Brown and Brown Banded cockroaches as well as palmettos.

Isobornyl acetate is a known lure. In the present invention, it has been discovered that santalol is a lure for cockroaches and palmettos and that isobornyl acetate and santalol are a synergistic combination as a lure.

Boric acid, boric oxide, calcium borate and sodium borate individually or in any combination are known blatticides. In the present invention, it has been discovered that their effectiveness is greatly enhanced when they are used in admixture with pyrogenic silica, pyrogenic titania or pyrogenic alumina. These materials, only when pyrogenic, act as highly effective electrostatic agents which cause the blatticide to cling to the cockroaches or palmettos. The proportion of these pyrogenic compounds relative to the boron containing compounds is preferably about 1:100 to about 5:100 by weight.

Other known insecticides may be used, including pyrethrum, pyrethrin I, pyrethrin II, permethrin and bioresmethrin. With the insecticide, there may be used such a synergist or adjuvant as piperonyl butoxide which increases the effectiveness of the insecticide, in particular, pyrethrum and pyrethrins. While cockroaches generally avoid insecticides other than boric acid and related borates, in the present invention it has been discovered that propyl cyclo hexyl acetate in combination with any of the aforementioned insecticides attracts the German cockroaches and that the addition of santalol, especially together with isobornyl acetate, attracts the other aforementioned cockroaches and palmettos. Particularly preferred among the non-boron-based insecticides is permethrin.

DETAILED DESCRIPTION OF PREFERRED EMBODIMENTS

Propyl cyclo hexyl acetate (formula (I) hereinbelow) may be synthesized by any of a number of methods, seven different ones of which are as follows:

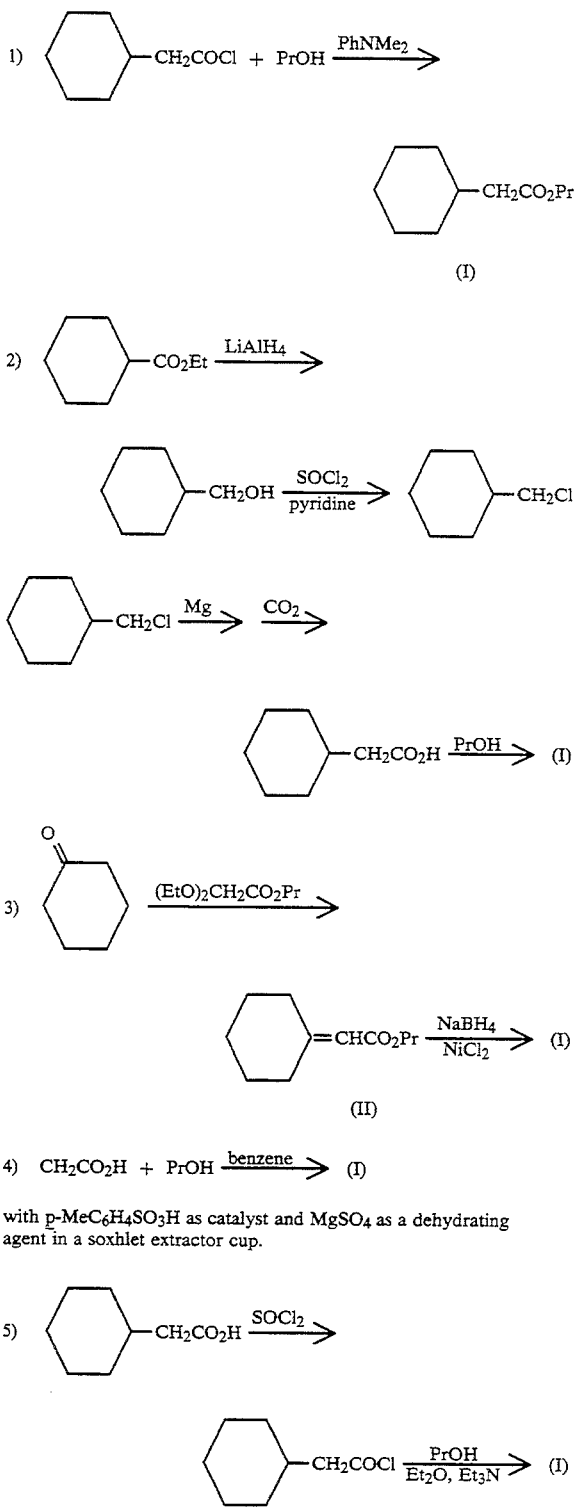

with $p\text{-MeC}_6H_4SO_3H$ as catalyst and $MgSO_4$ as a dehydrating agent in a soxhlet extractor cup.

6) 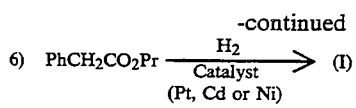

7) 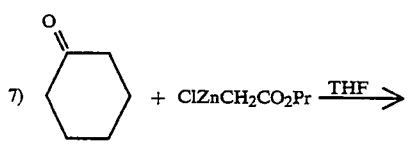

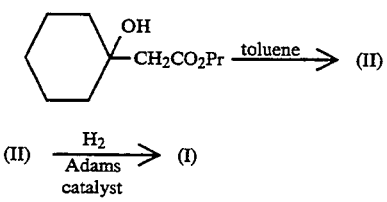

The term "aggregation" pheromone is understood to denote a pheromone which attracts male as well as female insects. Most pheromones attract only the females. Obviously, an aggregation pheromone can be used to more quickly eliminate an infestation.

Particularly effective powder or tablet baits which lure and kill Oriental, Smokey Brown, American and Brown Banded cockroaches as well as palmettos have formulations within the following parameters:

TABLE 1

| | Ingredient | Proportion, by weight |
|---|---|---|
| (1) | Boric acid, calcium borate, sodium borate or boric oxide, individually or in any combination of two or three (as blatticide) | 90–98% |
| (2) | Pyrogenic silica, titania or alumina as electrostatic agent, individually or in any combination | 1–5% |
| (3) | Isobornyl acetate and santalol (as lures for Oriental, Smokey Brown, American, Brown Banded cockroaches as well as palmettos) | 0.01–0.5% |
| (4) | Propyl cyclo hexyl acetate (as aggregation pheromone for German cockroach) | 0.01–0.5% |
| (5) | Magnesium stearate, calcium stearate or stearic acid (as lubricant) | 0.05 to 2% |
| (6) | Peanut flour and/or corn flour with antioxidant (as a bait) | 1 to 5% |

Ingredients (3) and (4) of the above mixture may be microencapsulated for time release purposes. Ingredients (3), (4) and (6), individually or as a mixture, may be microencapsulated for time release purposes and placed at the center of or be suspended above a tacky board to attract the cockroaches and palmettos to the board, where they are trapped by adhesion. The tackiness is provided by a coating of adhesives, gums and the like. Alternatively, the pheromones may be incorporated in the coating.

The antioxidants usually used with the peanut flour and/or corn flour are butylated hydroxyanisole ("BHA"), butylated hydroxytoluene ("BHT") or mono-tertiary-butyl hydroquinone ("TBHQ or "MTBHQ").

The above mixture may be formulated into a paste by diluting the blatticide powder with a humectant such as sorbitol and the like.

Particularly effective aerosol baits which lure and kill Oriental, Smokey Brown, American and Brown Banded cockroaches as well as palmettos have formulations within the following parameters:

TABLE 2

| | Ingredient | Proportion, by weight |
|---|---|---|
| (1) | Pyrethrum, pyrethrin I, pyrethrin II, permethrin or bio-resmethrin as the active insecticide (blatticide) | 0.01–5% |
| (2) | Piperonyl butoxide (as an adjuvant) | 0.05–2% |
| (3) | Pyrogenic silica, titania or alumina (as electrostatic agent) | 0.1–1% |
| (4) | Propyl cyclo hexyl acetate (as aggregation pheromone for German cockroach) | 0.01–0.1% |
| (5) | Isobornyl acetate and santalol (as lures) | 0.01–0.1% |
| (6) | Dimethyl ether or, if permitted by law, halocarbons (as aerosol propellant) | Balance |

The isobornyl acetate and santalol are generally used in a 60:40 proportion, by weight, but can be used in essentially any proportion. While in practice, santalol food chemical Codex (FCC) grade has been used, it is believed that both the alpha and beta forms of santalol work equally well.

In Table 2, for ingredient (6) there may be substituted a solvent, so that a pump aerosol may be used without any propellant. Solvents that can be used include alcohols, glycols, DMSO, water, ethers, ketones or any other solvents that lend themselves to use in particular types of containers.

In Table 2, instead of the blatticides there listed there may be used any other of many insecticides which are effective against cockroaches, such as chlorpyrifos, phosphorthioic acid O,O-diethyl O-[6-methyl-2-(1-methylethyl)-4-pyrimidinyl] ester (registered trademark "Diazinon" of Geigy), dimethyl dichlorovinylphosphate ("DDVP"), dichlorvos (sold, for example, under the Shell trademark "Vapona"), phosmet, malathion, carbaryl (sold, for example, under the Union Carbide trademark "Sevin"), methomyl, propoxur (sold under various trademarks, including "Sendran"), crotoxyphos (sold, for example, under the Shell trademark "Ciodrin"), and dioxatrion (sold, for example, under the Hercules trademark "Delnav").

Some specific illustrative examples of formulations according to the invention are as follows:

| Formula 1 (Powder or Tablets) | |
|---|---|
| Ingredient | Proportion, by weight |
| boric acid | 94.87% |
| pyrogenic silica | 2% |
| isobornyl acetate and santalol (60:40, by weight) | 0.02% |
| propyl cyclo hexyl acetate | 0.01% |
| lubricant (see (5) in Table 1) | 0.1% |
| bait (corn flour) | 3% |

| Formula 2 (Aerosol) | |
|---|---|
| Ingredient | Proportion, by weight |
| permethrin | 1% |
| piperonyl butoxide | 0.3% |
| pyrogenic silica | 0.2% |
| propyl cyclo hexyl acetate | 0.01% |
| isobornyl acetate and | 0.02% |

-continued

| Formula 2 (Aerosol) | |
|---|---|
| Ingredient | Proportion, by weight |
| santalol dimethyl ether | 98.47% |

As illustratively mentioned above, compounds, mixtures and formulations within the scope of the present invention may be used in conventional cockroach traps, such as tacky boards or tunnel or maze traps.

What is claimed is:

1. A mixture comprising propyl cyclo hexyl acetate and a blatticide.

2. A mixture comprising isobornyl acetate, santalol and a blatticide.

3. A mixture according to claim 2, further comprising propyl cyclo hexyl acetate.

4. A Mixture comprising at least one boron containing compound selected from the group consisting of boric acid, boric oxide, calcium borate and sodium borate and at least one pyrogenic compound selected from the group consisting of pyrogenic silica, pyrogenic titania and pyrogenic alumina.

5. A mixture according to claim 4, in which the weight ratio of the pyrogenic compound to the boron containing compound is in the range of about 1:100 to 5:100.

6. A powder of tablet bail for luring and killing Oriental, Smokey Brown, American and Brown Banded cockroaches and palmettos, comprising, by weight,
   90-98% of a blatticide selected from the group consisting of boric acid, boric oxide, calcium borate and sodium borate,
   1-5% of an electrostatic agent selected from the group consisting of pyrogenic silica, pyrogenic titania and pyrogenic alumina,
   0.01-0.5% of a lure comprising isobornyl acetate and santalol,
   0.01-0.05% of propyl cyclo hexyl acetate,
   0.05 to 2% of a lubricant, and
   1 to 5% of a bait.

7. An aerosol bait for luring and killing Oriental, Smokey Brown, American and Brown Banded cockroaches and palmettos, comprising, by weight,
   0.01-5% of a blatticide,
   0.05-2% of piperonyl butoxide,
   0.1-1% of an electrostatic agent selected from the group consisting of pyrogenic silica, pyrogenic titania and pyrogenic alumina,
   0.01-0.1% of propyl cyclo hexyl acetate,
   0.01-0.1% of a lure comprising isobornyl acetate and santalol,
   and the balance an aerosol propellant.

8. An aerosol bait according to claim 7, in which the blatticide is selected form the group consisting of pyrethrum, pyrethrin I, pyrethrin II, permethrin and bioresmethrin.

* * * * *